United States Patent
Kawai et al.

Patent Number: 5,541,193
Date of Patent: Jul. 30, 1996

[54] HETEROCYCLE-CONTAINING MACROCYCLIC IMMUNOMODULATORS

[75] Inventors: Megumi Kawai; Yat S. Or; Jay R. Luly, all of Libertyville, Ill.

[73] Assignee: Abbott Laboratories, Abbott Park, Ill.

[21] Appl. No.: 466,302

[22] Filed: Jun. 6, 1995

Related U.S. Application Data

[63] Continuation of Ser. No. 212,473, Mar. 14, 1994, abandoned, which is a continuation-in-part of Ser. No. 32,958, Mar. 17, 1993, abandoned, which is a continuation-in-part of Ser. No. 755,208, Sep. 5, 1991, abandoned.

[51] Int. Cl.$^6$ .................. C07D 491/18; A61K 31/395
[52] U.S. Cl. ................... 514/291; 514/411; 540/456
[58] Field of Search ............................ 514/211, 291; 540/456

[56] References Cited

U.S. PATENT DOCUMENTS

| | | | |
|---|---|---|---|
| 5,208,241 | 5/1993 | Ok et al. | 540/456 |
| 5,262,533 | 11/1993 | Sinclair et al. | 540/456 |

FOREIGN PATENT DOCUMENTS

| | | | |
|---|---|---|---|
| 0428365 | 5/1991 | European Pat. Off. | 540/456 |
| WO92/20688 | 11/1992 | WIPO | 540/456 |

*Primary Examiner*—Robert T. Bond
*Attorney, Agent, or Firm*—Steven R. Crowley; Gregory R. Steele

[57] ABSTRACT

Immunomodulatory macrocyclic compounds having the formula

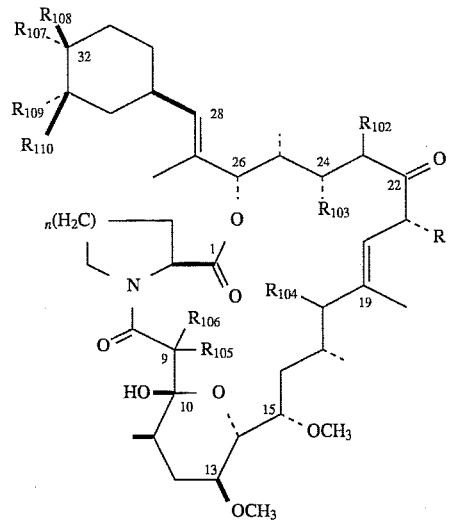

and pharmaceutically acceptable salts, esters, amides and prodrugs thereof, wherein one of $R^{107}$, $R^{108}$, $R^{109}$ and $R^{110}$ is a radical having the formula

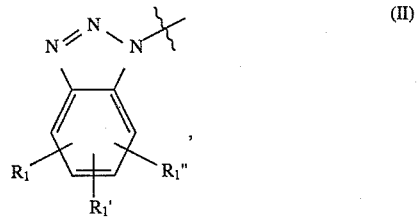

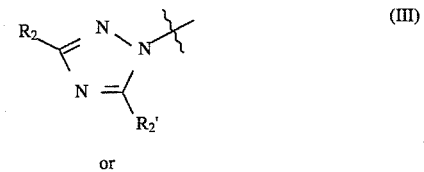

or

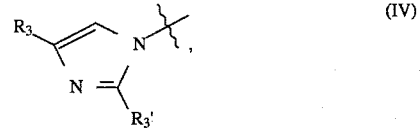

as well as pharmaceutically compositions containing such compounds and methods of immunomodulatory therapy utilizing the same.

19 Claims, No Drawings

HETEROCYCLE-CONTAINING MACROCYCLIC IMMUNOMODULATORS

This application is a continuation of U.S. patent application Ser. No. 08/212,473, filed Mar. 14, 1994, abandoned, which is a continuation-in-part of U.S. patent application Ser. No. 08/032,958, filed Mar. 17, 1993, which is a continuation-in-part of International Patent Application No. PCT/US92/07600, filed Sep. 8, 1992, which is a continuation-in-part of U.S. patent application Ser. No. 07/755,208, filed Sep. 5, 1991 and now abandoned.

FIELD OF THE INVENTION

The present invention relates to novel chemical compounds having immunomodulatory activity, and in particular to macrolide immunosuppressants. More particularly, the invention relates to semisynthetic analogs of ascomycin and FK-506, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. Immunosuppressant FK-506, isolated from a strain of *S. tsukubaensis*, is a 23-membered macrocyclic lactone represented by formula 1a, below. Other related natural products, such as FR-900520 (1b) and FR-900523 (1c), which differ from FK-506 in their alkyl substituent at C-21, have been isolated from *S. hygroscopicus yakushirnnaensis*. Yet another analog, FR-900525, produced by *S. tsukubaensis*, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

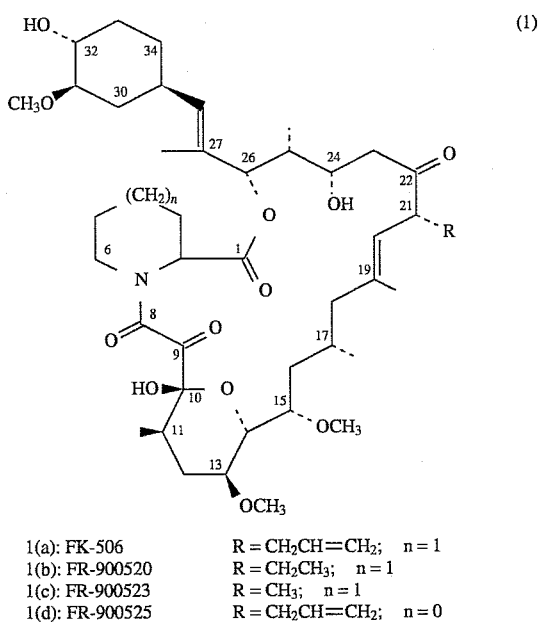

| | | |
|---|---|---|
| 1(a): FK-506 | R = CH$_2$CH=CH$_2$; | n = 1 |
| 1(b): FR-900520 | R = CH$_2$CH$_3$; | n = 1 |
| 1(c): FR-900523 | R = CH$_3$; | n = 1 |
| 1(d): FR-900525 | R = CH$_2$CH=CH$_2$; | n = 0 |

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ting-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ting by two carbons; and modifications which include methyl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds having the formula

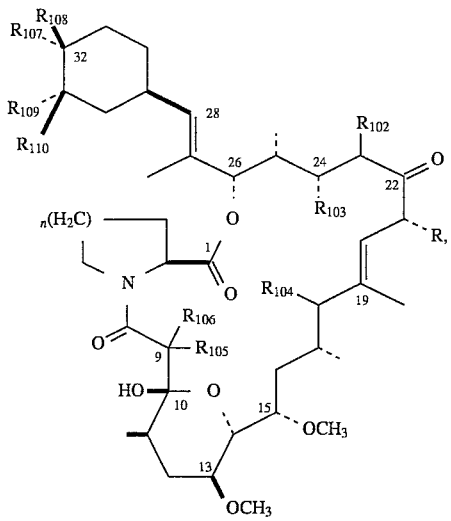
(I)

as well as pharmaceutically acceptable salts, esters, amides and prodrugs thereof. In the above formula (I), n is an integer between one and three, inclusive;

R is methyl, ethyl, allyl or propyl;

$R^{102}$ is hydrogen and $R^{103}$ is hydrogen, hydroxy or protected hydroxy, or, alternatively, $R^{102}$ and $R^{103}$ taken together to form a bond;

$R^{104}$ is hydrogen, hydroxy or protected hydroxy;

one of $R^{105}$ and $R^{106}$ is hydrogen and the other is hydroxy, or, alternatively, $R^{105}$ and $R^{106}$ taken together form a divalent radical selected from oxygen and methylene;

$R^{107}$, $R^{108}$ and $R^{110}$ are each independently hydrogen, methoxy or an azole radical; and $R^{109}$ is hydrogen or an azole radical.

Radicals $R^{107}$, $R^{108}$, $R^{109}$ and $R^{110}$ are subject to three provisos, namely, that (a) exactly one of $R^{107}$, $R^{108}$, $R^{109}$ and $R^{110}$ is an azole radical, (b) exactly one of $R^{107}$ and $R^{108}$ is hydrogen, and (c) exactly one of $R^{109}$ and $R^{110}$ is hydrogen.

The azole radical above is a 1,2,3-benztriazole, a 1,2,4-triazole or an imidazole selected from among the subformulae

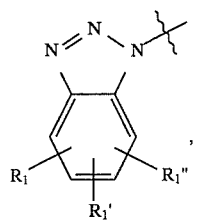
(II)

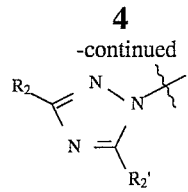
(III)

and

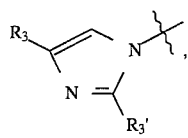
(IV)

in which $R^1$, $R^{1'}$ and $R^{1''}$ are independently:
(i) hydrogen,
(ii) lower alkyl,
(iii) lower alkenyl,
(iv) cycloalkyl,
(v) cycloalkylalkyl,
(vi) cycloalkylalkenyl,
(vii) nitro,
(viii) halogen,
(ix) —C(O)—O—$R^4$, where $R^4$ is hydrogen, loweralkyl or (c) arylalkyl,
(x) mono-, di-, tri-, or perhalogenated loweralkyl,
(xi) aryl, or
(xii) arylalkyl;
alternatively, any two adjacent $R^1$, $R^{1'}$ and $R^{1''}$ taken together with the carbon atoms to which they are attached may form a saturated or unsaturated carbocyclic or heterocyclic ring having between five and seven ring atoms, inclusive, and zero, one or two additional heteroatoms selected from nitrogen, oxygen and sulfur.

$R^2$ and $R^{2'}$ in the above subformulae are independently:
(i) hydrogen,
(ii) lower alkyl,
(iii) lower alkenyl,
(iv) amino,
(v) alkylamino,
(vi) arylalkylamino,
(vii) acylamino,
(viii) arylamino,
(ix) cycloalkyl,
(x) cycloalkylalkyl,
(xi) Cycloalkylalkenyl,
(xii) —C(O)—O—$R^4$ where $R^4$ is as described above,
(xiii) ureido,
(xiv) aryl,
(xv) arylalkyl,
(xvi) heterocyclic alkylamino, or
(xvii) nitro;
and $R^3$ and $R^{3'}$ are independently:
(i) hydrogen,
(ii) lower alkyl,
(iii) hydroxyalkyl,
(iv) alkoxyalkyl,
(v) halogen,
(vi) cyanoalkyl,
(vii) acylaminoalkyl,
(viii) alkylamino, (ix) arylalkylamino, (x) acylamino, (xi) arylamino, (xii) cycloalkyl, (xiii) cycloalkylalkyl, (xiv) aryl, or (xv) arylalkyl.

Representative of the compounds of the invention are those in which:

(a) R is ethyl;
(b) $R^{102}$ is hydrogen;
(c) $R^{103}$ is selected hydrogen or hydroxy;
(d) $R^{103}$ is protected hydroxy;
(e) $R^{104}$ is hydrogen or hydroxy;
(f) $R^{105}$ and $R^{106}$, taken together, form an oxo (=O) group; and/or
(g) n is one or two.

Preferred among the compounds of the present invention are those in which the heterocyclic radical is a 1,2,3-benztriazole or 1,2,4-triazole radical having the subformula:

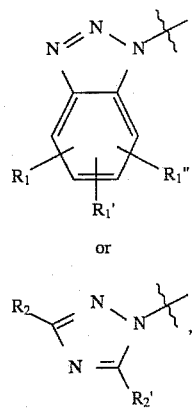

respectively. Of these, especially preferred are those compounds of subformula (III) in which $R^2$ and $R^{2'}$ are each hydrogen.

Compounds which are further representative of the present invention are the title compounds of Examples 1–60 which follow, and especially those of Examples 5–16.

In a second aspect of the present invention are disclosed pharmaceutical compositions useful for immunomodulation, comprising a therapeutically effective amount of a compound of the invention in combination with a pharmaceutically acceptable carrier.

In another aspect of the present invention is disclosed method of producing immunomodulation in a human or mammalian patient in need of such treatment, comprising administering to the patient a therapeutically effective amount of a compound of the invention in such amounts and for such time as is necessary to obtain the desired effect.

In yet another aspect of the present invention are disclosed processes for the preparation of the above compounds, as further described in connection with the examples which follow.

DETAILED DESCRIPTION OF THE INVENTION

The compounds of the present invention are those in which a single azole radical is substituted for either the C-31 methoxy functionality or the C-32 hydroxy functionality. In each instance, the azole substituent may be in either the R- or the S-configuration. Consequently, and in accordance with the provisos above, the possible configurations of these radicals $R^{107}$, $R^{108}$, $R^{109}$ and $R^{110}$ can be represented by the following partial structural formulae:

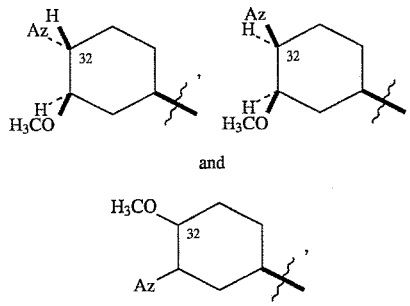

in which Az represents the azole radical as defined above.

As used throughout this specification and in the appended claims, the following terms have the meanings specified:

The term "acyl" as used herein refers to an aryl or alkyl group, as defined below, appended to a carbonyl group including, but not limited to, acetyl, pivaloyl, benzoyl and the like.

The term "acylamino" as used herein refers to an acyl group, as defined above, appended to an amino group including, but not limited to, acetylamino, pivaloylamino, benzoylamino and the like.

The term "acylaminoalkyl" as used herein refers to an acylamino group, as defined above, appended to an alkyl group, as defined below, including but not limited to, acetylamino methyl, acetylaminoethyl, propionylaminoethyl, and the like.

The term "alkenyl" as used herein refers to straight or branched chain groups of 2 to 12 carbon atoms containing one or more carbon-carbon double bonds including, but not limited to ethenyl, 1-propenyl, 2-propenyl, 2-methyl-1-propenyl, 1-butenyl, 2-butenyl and the like.

The term "alkoxy" as used herein refers to a loweralkyl, as defined below, attached to the remainder of the molecule through an oxygen atom including, but not limited to, methoxy, ethoxy, isopropoxy, n-butoxy, sec-butoxy, isobutoxy, tert-butoxy, and the like.

The term "alkoxyalkyl" as used herein refers to an alkoxy group, as defined above, appended to an alkyl group, as defined below.

The term "alkyl" as used herein refers to a monovalent straight chain or branched chain group of 1 to 12 carbon atoms including, but not limited to, methyl, ethyl, n-propyl, isopropyl, n-butyl, sec-butyl, isobutyl, tert-butyl and the like.

The terms "alkylamino" as used herein refers to a group having the structure —NH—(loweralkyl), where the loweralkyl portion is as defined below. Alkylamino and loweralkylamino groups include, for example, methylamino, ethylamino, isopropylamino and the like.

The terms "aryl" as used herein refers to carbocyclic aromatic groups including, but not limited to, phenyl, 1- or 2-naphthyl, fluorenyl, (1,2)-dihydronaphthyl, (1,2,3,4)-tetrahydronaphthyl, indenyl, indanyl and the like, substituted by $R^6$, $R^7$ and $R^8$.

The term "arylalkyl" as used herein refers to an aryl group, as previously defined, appended to an alkyl group including, but not limited to, benzyl, 1- and 2-naphthylmethyl, halobenzyl, alkoxybenzyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "arylalkylamino" as used herein refers to a group having the structure —NH—(arylalkyl), where the arylalkyl portion is as previously defined. Examples of arylalkylamino groups include benzylamino, 1-phenylethylamino and the like.

The term "arylamino" as used herein refers to an aryl group, as defined above, appended to an amino group including, but not limmitted to, anilino, naphthylamino and the like.

The term "cycloalkyl" as used herein refers to cyclic groups of 3 to 8 carbons including, but not limited to, cyclopropyl, cyclobutyl, cyclopentyl, cyclohexyl and the like.

The term "cyanoalkyl" as used herein refers to a cyano group appended to an alkyl group, as previously defined.

The term "cycloalkylalkenyl" as used herein refers to cycloalkyl, as defined above, appended to an alkenyl group, as defined above.

The term "cycloalkylalkyl" as used herein refers to a cycloalkyl group appended to a lower alkyl group including, but not limited to, cyclohexylmethyl and cyclohexylethyl.

The term "halogen" as used herein refer to an atom selected from fluorine, chlorine, bromine and iodine.

The term "heterocyclic" as used herein, except where otherwise specified, refers to any aromatic or non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 3 double bonds, (ii) the nitrogen and sulfur heteroatoms as well as the carbon atoms may optionally be oxidized by unsaturation and/or substitution by hydroxy, thiol, oxo or thiooxo, (iii) the nitrogen heteroatom may optionally be quaternized, (iv) any of the above heterocyclic rings may be fused to a benzene ring, and (v) any carbon or heteroatom with suitable valence may be optionally substituted. Representative heterocycles include, but are not limited to, pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrimidinyl, pyridazinyl, xanthenyl, xanthonyl, xanthopterinyl, oxazoyl, oxazolidinyl, thiouracilyl, isoxazolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thyminyl, benzimidazolyl, benzothiazolyl, benzoxazolyl, furyl, thienyl and benzothienyl.

The term "(heterocyclic)alkyl" as used herein refers to a heterocyclic group appended to an alkyl group, as previously defined.

The term "(heterocyclic)alkylamino" as used herein refers to a (heterocyclic)alkyl moiety, as defined above, attached via an amino group.

The term "hydroxyalkyl" as used herein refers to a hydroxy group appended to an alkyl group, as previously defined.

The term "hydroxy-protecting group" as used herein refers to those groups which are known in the art of organic synthesis (Greene, T. W. and Wuts, P. G. M., Protective Groups in Organic Synthesis, 2nd Ed., John Wiley & Son, Inc., 1991) to protect a hydroxy group against undesirable reaction during synthetic procedures and to be selectively removable including, but not limited to, methylthiomethyl, dimethylthexylsilyl, trisubstituted silyl such as tri(lower) alkylsilyl (e.g. trimethylsilyl, triethylsilyl, tributylsilyl, tri-i-propylsilyl, tert-butyldimethylsilyl, tri-tert-butylsilyl, triphenylmethyl-dimethylsilyl, etc.); lower alkyldiarylsilyl (e.g. methyl-diphenylsilyl, ethyl-diphenylsilyl, propyl-diphenylsilyl, tert-butyl-diphenylsilyl, etc.), and the like; triarysilyl (e.g. triphenylsilyl, tri-p-xylylsilyl, etc.); triarylalkylsilyl (e.g. tribenzylsilyl, etc.); alkylacyl (e.g. acetyl); aryloyl (e.g. benzolyl); alkoxycarbonyl (e.g. ethoxycarbonyl); -S(O)$_2$-(loweralkyl),-S(O)$_2$-(aryl); acyl substituted with an aromatic group and the like.

The term "lower alkyl" as used herein refers to an alkyl group, as defined above, of 1 to 8 carbon atoms.

The term "lower alkenyl" as used herein refers to an alkenyl group, as defined above, of 2 to 8 carbon atoms.

The term "mono, di, tri, or perhalogenated lower alkyl" as used herein refer to a lower alkyl group as defined above, substituted with one or more halogens, including, but not limited to chloromethyl, trifluoromethyl, 2,2,2-trichloroethyl, and the like.

The term "oxo" as used herein refers to an oxygen atom forming a carbonyl group.

The term "protected hydroxy" as used herein refers to a hydroxy group to which has been appended a hydroxy-protection group, as previously defined.

The term "ureido" as used herein refers to a radical having the formula —NHC(O)NH$_2$.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," J. pharm. Sci., 66: 1–19 (1977) which is incorporated herein by reference.)

Examples of pharmaceutically acceptable, non-toxic esters of the compounds of this invention include $C_1$ to $C_6$ alkyl esters wherein the alkyl group is a straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Preferred prodrugs include:

(a) acyloxymethyl esters of carboxylic acids, for example, —C(O)—O—CH$_2$—O—C(O)—t—Bu, —C(O)—O—CH(CH$_3$)—O—C(O)—OCH$_2$CH$_3$ or —C(O)—O—Re wherein Re is

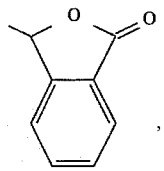

and the like;

(b) (5-methyl-2-oxo-1,3-dioxolen-4-yl)methyl esters of carboxylic acids;

(c) esters derived from alcohol groups in the parent drug by reaction with succinic acid, phosphoric acid, dialkylaminoacetic acid or an amino acid, for example, —O—C(O)—R$^f$ wherein R$^f$ is (CH$_3$)$_2$NCH$_2$—, NH$_2$CH$_2$—, n-PrNHCH$_2$—, NH$_2$CH$_2$CH$_2$—, (CH$_3$)$_2$NCH$_2$CH$_2$—, (CH$_3$)$_2$NCH$_2$CH$_2$CH$_2$—, N-morpholinylmethyl, N-methyl-N'-piperazinylmethyl, phenyl, CH$_3$CH$_2$CH$_2$—, CH$_3$CH$_2$CH$_2$CH$_2$— or HO(O)CCH$_2$CH$_2$—, and the like;

(d) N-Mannich bases of amides or amines, for example, —C(O)—NH—CH$_2$R$^c$ or —NH—CH$_2$R$^c$ wherein R$^c$ is piperidin-1-yl, morpholin-1-yl, N-phenethylamino, N-phenylpropanolamino, N-methylamino, N-ethylamino, N,N-diethylamin, N,N-dimethylamino, HO(O)C—CH(CH$_3$)—NH—, phenyl—NH— or p—CH$_3$—phenyl—NH—, and the like;

(e) N-hydroxymethyl derivatives of amides, for example, —C(O)—NH—CH$_2$OH;

(f) N-acyloxyalkyl derivatives of amides or heterocyclic amines, for example, —C(O)—NH—Rg or =N—Rg wherein Rg is acetoxymethyl, butyryloxymethyl, benzoyloxymethyl, nicotinoyloxymethyl, N,N-dimethylglycyloxymethyl, N,N-diethylglycyloxymethyl, N,N-dipropylgylcyloxymethyl, phenylalanyloxymethyl, leucyloxymethyl, phenylglycyloxymethyl or N,N-diethylalanyloxymethyl, and the like;

(g) oxazolidinones derived from ketone groups in the parent drug by reaction with 2-aminoethanol, N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol, and the like; and (h) enol esters derived from ketone groups in the parent drug, for example, acetyl enol esters, propionyl enol esters, butyryl enol esters, isobutyryl enol esters, pivaloyl enol esters, benzoyl enol esters or N,N-dimethylglycyl enol esters, and the like.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, cyanomethyl ester method and the like), the Woodward reagent K method, the DCCHOBT (1-hydroxy-benzotriazole) method and the like. Classical methods for amino acid condensation reactions are described in "Peptide Synthesis" Second Edition, M. Bodansky, Y. S. Klausnet and M. A. Ondetti (1976).

As in conventional peptide sysnthesis, branched chain amino and carboxyl groups at alpha and omega positions in amino acids may be protected and deprotected if necessary. The protecting groups for amino groups which can be used involve, for example, benzyloxycarbonyl (Z), o-chlorobenzyloxycarbonyl ((2-Cl)Z)), p-nitrobenzyloxycarbonyl (Z(NO$_2$)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

Numerous asymmetric centers may exist in the compounds of the present invention. Except where otherwise noted, the present invention contemplates the various stereoisomers and mixtures thereof. Accordingly, whenever a bond is represented by a wavy fine, it is intended that both steric orientations are intended.

The compounds of the invention, including but not limited to those specified in the examples, possess immunomodulatory activity in animals. As immunosuppressants, the compounds of the present invention may be useful for the treatment and prevention of immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucosa and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali bum; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, antiinflammatory activity, and so on.

Additionally, some compounds appear to possess FK-506 antagonistic properties. The compounds of the present invention may thus be used in the treatment of immunodepression or a disorder involving immunodepression. Examples of disorders involving immunodepression include AIDS, cancer, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13, 19,21, 27-tetramethyl-11,28-dioxa-4-azatricyclo[22.3.1.0$^{4,9}$]octacos-18-ene such as FK-506, or rapamycin. Overdosing of such medicants by patients is quite common upon their realizing that they have forgotten to take their medication at the prescribed time and can lead to serious side effects.

A further situation in which the compounds of the present invention may be used to treat immunosuppression is in vaccination. It is sometimes found that the antigen introduced into the body for the acquisition of immunity from disease acts as an immunosuppressive agent, and so antibodies are not produced by the body and immunity is not acquired. By introducing a compound of the invention into the body (as in a vaccine), the undesired immunosuppression may be overcome and immunity acquired.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat gastrointestinal disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the an to start doses of the compound at levels lower than required for to achieve the desired therapeutic effect and to gradually increase the dosage until the desired effect is achieved.

The total daily dose of the compounds of this invention administered to a human or lower animal may range from about 0.00 1 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is deskable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly-(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredient in finely divided form may be used in admixture with a larger-sized pharmaceutically acceptable inert carder comprising particles having a size, for example, of up to 100 micrometers in diameter. Suitable inert carders include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as automimmue diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more of the processes which follow. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, Novel immunosuppressants isolated from *A streptomyces*. I. Taxonomy of the producing strain. J. Antibiot., 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, Novel immunosuppressants isolated from *A streptomyces*. II Fermentation, isolation and physico-chemical and biological characteristics. J. Antibiot., 1988. XLI(11), 1592–1601; (iii) T. Arai, Y. Koyama, T. Suenaga and H. Honda, Ascomycin, An Antifungal Antibiotic. J. Antibiot., 1962. 15(231–2); and (iv) T. Arai in U.S. Pat. No. 3,244,592. One or more of the processes discussed below may be then employed to produce the desired compound of the invention.

Such processes comprise:

(a) producing a compound of formula I, which contains bis(CH—O—PG) groups, in a corresponding compound wherein PG is a protecting group.

(b) producing a compound of formula I, which contains a mono(CH—O—PG) group, by selective deprotection in a corresponding compound wherein PG is a protecting group.

(c) producing a compound of formula I, which contains a CH—OLG group, by selective activation of a selected CH—OH group in a corresponding compound wherein —OLG is a leaving group which is easily displaced by nucleophilic attack.

(d) producing a compound of formula I, which contains a CH—$R^{100}$ group, by selective displacement of a selected CH—OLG group in a corresponding compound wherein —$R^{100}$ is a nucleophile.

(e) producing a compound of formula I, which contains a CH—OH group, by selective and final deprotection of a CH—O—PG in a corresponding compound.

(f) producing a compound of formula I, which contains a CH—OSO$_2$F group, by selective activation of a CH—OH group with an appropriate amount of fluorosulfonyl anhydride under conditions suitable for the production of the desired product;

(g) producing a compound of formula I, which contains a CH—OH group with inverted stereochemistry, by first activating a selected CH—OH group to its corresponding sulfonate, examples are but not limited to CH—OSO$_2$F and CH—OSO$_2$CF$_3$ and reacting with dimethylsulfoxide-water, or water with other cosolvents.

In process (a), the hydroxy group at C-24 position may or may not necessary to be protected. Suitable protecting groups for hydroxy, however, include those groups well known in the art such as dimethylthexylsilyl, trisubstituted silyl such as tri(lower)alkylsilyl (e.g. trimethylsilyl, triethylsilyl, tributylsilyl, tri-i-propylsilyl, tert-butyl-dimethylsilyl, tri-tert-butylsilyl, triphenylmethyl-dimethylsilyl, etc.); lower alkyldiarylsilyl (e.g. methyldiphenylsilyl, ethyldiphenylsilyl, propyl-diphenylsilyl, tert-butyl-diphenylsilyl, etc.), and the like; triarysilyl (e.g. triphenylsilyl, tri-p-xylylsilyl, etc.); triarylalkylsilyl (e.g. tribenzylsilyl, etc.), and the like, in which the preferred one may be tri($C_1$-to-$C_4$)alkylsilyl and $C_1$-to-$C_4$ alkyldiphenylsilyl, and the most preferred one may be tert-butyldimethylsilyl;

The suitable o-silylation reactions may be carried out using a wide variety of organosilicon reagents such as, but not limited to tert-butyldimethylsilyl chloride, N-(tert-butyldimethylsilyl)-N-methyltrifluoroacetamide (Mawhinney, T., and Madison, M. A. *J. Org. Chem.*, 1982, 47, 3336), tert-butylchlorodiphenylsilane ( Hanessian, S. and Lavallee, P *Can. J. Chem.*, 1975, 63, 2975), tert-butyldimethylsilyl trifluoromethanesulfonate ( Mander, L. N. and Sethi, S. P. *Tetrahedron Lett.*, 1984, 25, 5953), dimethylthexylsilyl chloride or dimethylthexylsilyl trifluoromethanesulfonate (Wetter, H. and Oertle, K. *Tetrahedron Lett.*, 1985, 26, 5515), 1-(tert-butyldimethylsilyl)-imidazole and the like.

Carbonates may be prepared by using a wide variety of a haloformates such as methy, ethyl, 2,2,2-trichloroethyl, isobutyl, vinyl, allyl, 2-(trimethylsilyl)ethyl, 2-(benzenesulfonyl)ethyl, 2-(trimethylsilyl)ethoxy methyl, benzyl and substituted benzyl chloroformates, where benzyl substituents include p-methoxy, 3,4-dimethoxy and p-nitro, in the presence of tertiary base such as pyridine, triethylamine, imidazole, diisopropylethylamine and the like. (*Tetrahedron Lett.*, 1980,21, 3343; ibid., 1981, 22, 3667; ibid. 1981,22, 969; ibid. 1981, 22, 1933.)

The reaction may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as imidazole, triethylamine or pyridine.

In process (b), suitable reagents for selective deprotection of a protecting group (PG) from CH—O—PG may be carefully carried out by using, but not limitted to, aqueous hydrogen fluoride in acetonitrile (Newton, R. F., Reynolds, D. P., Finch, M. A. W., Kelly, D. R. and Roberts, S. M. *Tetrahedron Lett.*, 1979, 3891), tetraalkyl ammonium fluoride in tetrahydrofuran (Corey, E. J. and Snider, B. B. *J. Am. Chem. Soc.*, 1972, 94, 2549, Corey, E. J. and Venkateswarlu, A. *J. Am. Chem. Soc.*, 1972, 94, 6190) or tetraalkyl ammonium chloride-potassium fluoride in acetonitrile (Carpino, L. A. and Sau, A. C. *J. Chem. Soc., Chern. Commun.* 1979, 514) wherein an alkyl group as defined above, p-toluenesulfonic acid, potassium carbonate in anhydrous methanol (Hurst, D. T. and MaInnes, A. G. *Can. J. Chem.*, 1965, 43, 2004), citric acid in methanol (Bundy, G. L. and Peterson, D. C. *Tetrahedron Lett.*, 1978, 41), acetic acid: water (3:1) (Corey, E. J. and Varma, R. K. *J. Am. Chem. Soc.*, 1971, 93, 7319), Dowex 50W-X8 in methanol (Corey, E. J., Ponder, J. W. and Ulrich, P. *Tetrahedron Lett.*, 1980, 21, 137), boron trifluoride etherate in chloroform (Kelly, D. R., Roberts, M. S. and Newton, R. F. *Synth. Commun.* 1979, 9, 295), methanolic hydrogen fluoride (Hanessian, S. and Lavallee, P. *Can. J. Chem.*, 1975, 53, 2975; ibid., 1977, 55, .562), and pyridinuim fluoride in tetrahydrofuran (Nicolaou, K. C., Seitz, S. P., Pavia, M. R. and Petasis, N. A. *J. Org. Chem.*, 1979, 44, 4011 ), pyridinium p-toluenesulfonate in ethanol (Prakash, C., Saleh, S. and Blair, I. A. *Tetrahedron Lett.*, 1989, 30, 19), N-bromo-succinimide in dimethylsulfoxide (Batten, R. J. et al., *Synthesis*, 1980, 34), and tetraethyldiboroxane in the presence of catalytic amounts of trimethylsilyl triflate (Dahlhoff, W. V. and Taba, K. M., *Synthesis*, 1986, 561).

The reaction is usually conducted under from cooling to heating, preferably from 0° C. to 50°C. The reaction may require 20 minutes to one day, depending on the reagent and temperature chosen.

In process (c), suitable reagents for activation of an alcohol include acetic anhydride, trifluoromethanesulfonic anhydride (triflic anhydride), fluorosulfonic anhydride, methanesulfonyl chloride (mesyl chloride), p-toluenesulfonyl chloride (tosyl chloride), trifluoroacetic anhydride, trifluoroacetyl chloride, o-nitrobenzenesulfonyl chloride, 1-methyl-2-fluoropyridinium salt and the like.

The activation may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as triethylamine or pyridine.

The reaction is usually conducted under from cooling to heating, preferably from −70° C. to 50° C. The reaction may require 20 minutes to one day, depend on the reagent and temperature chosen.

In process (d), a variety of compounds may be prepared from the displacement reactions. An activated hydroxy group such as CH—OSO$_2$CF$_3$ or CH—OSO$_2$F may be substituted by triazoles or imidazoles (as defined above and below). The displacement reaction may be carried out in a solvent which does not adversely affect the reaction (e.g. chloroform, dichloromethane, tetrahydrofuran, pyridine, dimethylsulfoxide, N,V-dimethylformamide, hexamethylphosphoramide, etc. or a mixture thereof). The reaction may be conducted above, at, or below ambient temperature, preferably from 0° C. to 50° C. The reaction may require 20 minutes to one week, depend on the reagent chosen.

In process (e), the final deprotection of a C-24 protecting group may be carded out according to the methods described in process (c).

In process (f), suitable reagent for activation of an alcohol of formula I is fluorosulfonic anhydride (prepared according to the procedure described by S. Kongpricha, W. G. Preusse and R. Schwarer, in *Inorganic Synthesis*, 1968, 11, 151–155). The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from −100° to 30° C., and more preferably from −78° to 0° C. The reaction may require 20 minutes to 24 hours to complete, depending on the reagent chosen.

In process (g), a suitable reagent for activation of an alcohol of formula I is sulfonyl chlorides, fluorosulfonic anhydride or trifluoromethanesulfonic anhydride. The activation may be carded out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from −100° to 30° C., and more preferably from −78° to 0° C. The reaction may require 20 minutes to 24 hours to complete, depending on the reagent chosen.

A suitable reagent for the inversion of stereochemistry is water, dimethylsulfoxide, pyridine N-oxide, dimethylphosphite or triphenylphosphine oxide. The inversion reaction may be carded out in a solvent which does not adversely affect the reaction (e.g. dioxane, tetrahydrofuran, dimethylsulfoxide or a mixture therof). The reaction may require cooling or heating, depending on the method used. The reaction temperature is preferably from −100° to 30° C., and more preferably from −78° to 0° C. The reaction may require 20 minutes to 24 hours to complete, depending on the reagent chosen.

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1:

Formula I: R=ethyl; $R^{102}$=H; $R^{103}$=$R^{107}$=tert-butyldimethylsilyloxy; $R^{104}$=H; $R^{105}$ and $R^{106}$ taken together form an oxo; $R^{108}$=$R^{109}$=H; $R^{110}$=methoxy; n=2.

Ascomycin (25 g, 0.032 mol) was dissolved in a solution of imidazole (43.03 g, 0.64 mmol) in dry N,N-dimethylformamide (500 mL) and tert-butyldimethylchlorosilane (47.64 g, 0.32 mol) was added in portions and stirred at room temperature for 24 hours. N,N-dimethylformamide and excess tert-butyldimethylchlorosilane were removed by evaporation (35° C. water bath) under high vaccum. The solid residue was dissolved in 350 mL of ethyl acetate, and the ethyl acetate layer was washed with saturated ammonium chloride aqueous solution (200 mL×3), 10%-NaHSO$_4$ (200 mL×3), brine, saturated NaHCO$_3$ ( 200 mL×3), and brine (200 mL×3). After dired over MgSO$_4$, solvent was removed invacuo and the solid residue was purified by silica gel chromatography, followed by HPLC eluting with 5% acetone in hexane providing the title compound (27 g) in 84% yield. MS (FAB) m/z: M+K=1058.

EXAMPLE 2:

Formula I: R=ethyl; $R^{102}$=H; $R^{103}$=tert-butyldimethylsilyloxy; $R^{104}$=H; $R^{105}$ and $R^{106}$ taken together form an oxo; $R^{107}$=hydroxy; $R^{108}$=$R^{109}$=H; $R^{110}$=methoxy; n=2.

To a solution of 48% hydrogen fluoride aqueous solution (5 mL) was added Example 1 (32 g, 0.031 mol) in acetonitrile (500 mL), and the mixture was stirred at room temperature for 90 minutes. It was cooled to 0° C. in an ice bath, and solid NaHCO$_3$ was added to the reaction mixture. It was stirred for 1 hour and solid was removed by filtration. Acetonirile was removed in vacuo and ethyl acetate (500 mL) was added to the residue, and the organic layer was washed with 10%-NaHCO$_3$ (300 mL×3), brine (250 mL), 10%-NaHSO$_4$ (300 mL×3), and brine (350 mL×3), and dried over anhydrous sodium sulfate. Evaporation of the solvent gave 35 g of crude title compound which was purified by silica gel column chromatography, followed by HPLC eluting with 25%-acetone in hexane. 24.28 g (85%) of pure compound was obtained. MS (FAB) m/z: M+K=844; In addition to the tilte compound, unreacted starting material (Example 1, 1.5 g) and ascomycin (500 mg) were isolated as a pure form.

EXAMPLE 3:

Formula I: R=ethyl; $R^{102}$=H; $R^{103}$=tert-butyldimethylsilyloxy; $R^{104}$=H; $R^{105}$ and R106 taken together form an oxo; $R^{107}$=O-trifluoromethanesulfonyl; $R^{108}$=$R^{109}$=H; $R^{110}$=methoxy; n=2.

The product of Example 2 (4.0 g, 4.42 mmol) was dissolved in 20 mL of methylene chloride at 0° C. Pyridine (3.57 mL, 44.2 mmol), followed by trifluoromethanesulfonic acid anhydride (0.74 mL, 4.42 mmol) were carefully added to the reaction mixture. It was stirred at 0° C. for 20 minutes and the solvent was removed. Ethyl acetate (50 mL) was added to the residue. The organic layers were washed with brine, saturated NaHCO$_3$ (20 mL×3), brine (20 mL), 10%-NaHSO$_4$ (20 mL×3), brine (20 mL×3) and dried over anhydrous sodium sulfate. After the solvent was removed, the title compound was obtained in quantitative yield (4.2 g). This compound was used for the displacement reaction without further purification and characterization.

EXAMPLE 4:

Formula I; R=ethyl; $R^{102}$=H; $R^{103}$=tert-butyldimethylsilyloxy; $R^{104}$=H; $R^{105}$ and $R^{106}$ taken together form an oxo; $R^{107}$=$R^{109}$=H; $R^{108}$=1-(1,2,3-triazolyl); $R^{110}$=methoxy; n=2.

The product of Example 3 (2.1 g, 2.03 mmol) was dissolved in 10 mL of freshly distilled methylene chloride, (1H)-1,2,3-triazole (0.42 g, 6.08 mmol) and triethylamine (0.565 mL, 4.05 mmol) were added, and the reaction was then stirred at room temperature for three days. The reaction mixture was passed through silica gel, using 10–25 % acetone in hexane as an elutant to obtain semi-pure title compound (1.25 g) in 65 % yield. MS (FAB) m/z: M+K= 995.

EXAMPLE 5:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,3-triazolyl); $R^{110}$=methoxy; n=2.

The product of Example 4 (1.25 g, 1.307 mmol) was dissolved in 35 mL of acetonitrile, 48% hydrogen fluoride aqueous solution (4 mL) was added, and the reaction was then stirred at room temperature for 4 hours. It was cooled to 0° C. in an ice bath, and solid NaHCO$_3$ was added to the reaction mixture. It was stirred for an additional 2 hours and solid was removed by filtration. Acetonirile was removed in vacuo and the residue was purified by high performance liquid chromatography (HPLC), eluting with 30% acetone in hexane. 263.6 mg of pure title compound was obtained in 24% yield. MS (FAB) m/z: M+K=881; mp=110°–113° C. (dec.); $^1$H-NMR (ppm in pyridine): 3.25 (s, 3H, R$^{1'}$-OMe)

EXAMPLE 6:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(1,2,3-triazolyl) and the other is hydrogen; n=2.

The title compound (85 mg) was isolated from the reaction described in Example 3 as a minor product in 8% yield. MS (FAB)m/z: M+K=881; mp=103°–105° C.; $^1$H-NMR (ppm in pyridine): 3.05 (s, 3H, R$^{1'}$-OMe)

EXAMPLE 7:

Formula I; R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,3-benzotriazolyl); $R^{110}$=methoxy; n=2.

Following the procedure of Example 4, but replacing (1H)-1,2,3-triazole with (1H)-1,2,3-benzotriazole, provided the desired compound. The product of Example 3 (2.1 g, 2.03 mmol), (1H)-1,2,3-benzotriazole (0.724 g, 6.08 mmol), and triethylamine (0.565 mL, 4.05 mmol) in 10 mL of methylene chloride were used and stirred at room temperature for three days. 1.45 g of pure compound was isolated after silica gel column chromatography, followed by normal phase HPLC purification in 71% yield. MS (FAB) m/z: M+H=1007. M+K=1045. The obtained product (1.4 g, 1.39 mmol) was treated with 48%-HF (4 mL) in 40 mL of acetonitrile in the procedure described in Example 5. After a normal phase-HPLC purification, 422 mg of the pure title compound was isolated in 34% yield. MS (FAB) m/z: M+K=931. mp=120° C.; $^1$H-NMR (ppm in pyridine): 3.15 (s, 3H, R$^{1'}$-OMe)

EXAMPLE 8

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(1,2,3-benzotriazolyl) and the other is hydrogen; n=2.

The title compound (60 mg) was isolated from the reaction described in Example 7 as a minor product in 5% yield. MS (FAB) m/z: M+K=931; mp=115°–116° C.; $^1$H-NMR (ppm in pyridine): 2.95 (s, 3H, R$^{1'}$-OMe)

EXAMPLE 9:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-nitro-1,2,3-benzotriazolyl); $R^{110}$=methoxy; n=2.

Following the procedure of Example 4, but replacing (1H)-1,2,3-triazole with 5-nitro-(1H)- 1,2,3-benzotriazole, provided the desired compound. The product of Example 3 (2.1 g, 2.03 mmol), 5-nitro-(1H)-1,2,3-benzotriazole (0.997 g, 6.08 mmol), and triethylamine (0.565 mL, 4.05 mmol) in 10 mL of methylene chloride were used and stirred at room temperature for three days. 2.0 g of semi-pure compound was isolated after silica gel column chromatography, followed by normal phase HPLC purification. MS (FAB) m/z: M+H=1090. The obtained product (2.0 g, 1.90 mmol) was treated with 48%-HF (4 mL) in 40 mL of acetonitrile in the procedure described in Example 5. After a normal phase-HPLC purification, 146.5 mg of the pure title compound was isolated in 8% yield. MS (FAB) m/z: M+K=976. mp=125°–130° C.; $^1$H-NMR (ppm in pyridine): 3.20 (s, 3H, R$^{1'}$-OMe), 7.99 (d, 1H, aromatic), 8.40 (d. 1H, aromatic).

EXAMPLE 10:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-nitro-1,2,3-benzotriazolyl); $R^{110}$=methoxy; n=2.

The title compound (80 mg) was isolated from the reaction mixture described in Example 9 as a minor product in 4% yield. MS (FAB) m/z: M+K=976. mp=120° C. (dec.); $^1$H-NMR (ppm in pyridine): 3.19 (s, 3H, R$^{1'}$-OMe), 8.20 (s, 1H, aromatic), 8.40 (br. d. 1H, aromatic), 8.99 (s, 1H, aromatic).

EXAMPLE 11:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-nitro-1,2,3-benzotriazolyl) and the other is hydrogen; n=2.

The title compound (78 mg) was isolated from the reaction described in Example 9 as a minor product in 4% yield. MS (FAB) m/z: M+K=976. mp=110°–117° C. (dec.); $^1$H-NMR (ppm in pyridine): 2.99 (s, 3H, R$^{1'}$-OMe), 7.95–8.02 (br. m. aromatic), 8.20 (m, aromatic).

EXAMPLE 12:

Formula I; R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-nitro-1,2,3-benzotriazolyl) and the other is hydrogen; n=2.

The title compound (78 mg) was isolated from the reaction described in Example 9 as a minor product in 4% yield. MS (FAB) m/z: M+K=976. mp=115° C. (dec.); $^1$H-NMR (ppm in pyridine): 2.99 (s, 3H, R$^{1'}$-OMe), 8.23 (m, aromatic).

EXAMPLE 13:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,4-triazolyl); $R^{110}$=methoxy; n=2.

Following the procedure of Example 4, but replacing (1H)-1,2,3-triazole with (1H)-1,2,4-triazole, provided the desired compound. The product of Example 3 (1.7 g, 1.67 mmol), (1H)-1,2,4-triazole (0.288 g, 4.18 mmol), and triethylamine (0.58 mL, 4.18 mmol) in 10 mL of methylene chloride were used and stirred at room temperature for one over night and at 40° C. for an additional day. After silica gel column chromatography eluting with 10%-acetone in hexane, followed by normal phase HPLC purification using 40% acetone in hexane as an elutant, 1.057 g of pure major isomer was isolated in 67% yield. MS (FAB) m/z: M+K= 995, M+H=957. An additional 0.28 g of minor isomer was isolated as a pure form in 18% yield. MS (FAB) m/z M+H=957. This minor isomer was used to prepare an example 14. The obtained major product (1.05 g, 1.106 mmol) was treated with 48 %-HF (4 mL) in 35 mL of acetonitrile in the procedure described in Example 5. After a reverse phase-HPLC purification, 190 mg of the pure title compound was isolated in 18% yield. MS (FAB) m/z: M+K=881, M+H=843. mp=110°–114° C.; $^1$H-NMR (ppm in pyridine): 8.20 (s, 1H, triazole), 8.80 (s. 1H, triazole). $^{13}$C-NMR (ppm in pyridine): 142.7 (t, CH, triazole), 143.2 (t. CH, triazole).

EXAMPLE 14:

Formula I: R=ethyl; $R^{102}$=H; $R^{103}$=hydroxy; $R^{104}$=H; $R^{105}$ and $R^{106}$ taken together form an oxo: one of $R^{107}$ or $R^{108}$=methoxy and the other is hydrogen; one of $R^{109}$ or $R^{110}$ is 1-(1,2,4-triazolyl) and the other is hydrogen; n=2.

The above minor product (example 13) (0.28 g, 0.292 mmol) was treated with 48%-HF (1 mL) in 10 mL of acetonitrile in the procedure described in Example 5, for three hours. After a reverse phase-HPLC purification, 52 mg of the pure title compound was isolated in 22 yield. MS (FAB) m/z: M+K=881, M+H=843. mp=92°–98° C.; $^1$H-NMR (ppm in pyridine): 8.25 (s, 2H, triazole). $^{13}$C-NMR (ppm in pyridine): 145.0 (t, 2-CH, triazole).

EXAMPLE 15:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-nitro- 1,2,4-triazolyl); $R^{110}$=methoxy; n=2.

Following the procedure of Example 4, but replacing (1H)- 1,2,3-triazole with 3-nitro-1,2,4-triazole, provided the desired compound. The product of Example 3 (2.0 g, 1.93 mmol), 3-nitro-1,2,4-triazole (0.66 g, 5.79 mmol), and triethylamine (0.538 mL, 3.86 mmol) in 10 mL of methylene chloride were used and stirred at room temperature for three days. 1.59 g of semi-pure compound was isolated after silica gel column chromatography, initally eluting with 10%-acetone in hexane, followed by 10% methanol in methylene chloride in 82% yield. MS (FAB) m/z: M+K=1040. The obtained product (1.58 g, 1.78 mmol) was treated with 48%-HF (4 mL) in 35 mL of acetonitrile in the procedure described in Example 5. After a normal phase-HPLC purification, 219 mg of the pure title compound was isolated in 16% yield. MS (FAB)m/z: M+K=926. mp=110°–112° C.; $^1$H-NMR (ppm in pyridine):3.24 (s, 3H, $R^{1'}$-OMe)

EXAMPLE 16:

Formula I: R=ethyl; $R^{102}$=H; $R^{103}$=hydroxy; $R^{104}$=H; $R^{105}$ and $R^{106}$ taken together form an oxo; one of $R^{107}$ or R108=methoxy and the other is hydrogen; one of $R^{109}$ or $R^{110}$ is 1-(3-nitro-1,2,4-triazolyl) and the other is hydrogen; n=2.

The title compound (98 mg) was isolated from the reaction described in Example 15 as a minor product in 7% yield. MS (FAB) m/z: M+K =926; mp=121°–127° C.; $^1$H-NMR (ppm in pyridine): 3.01 (s, 3H, $R^1$-OMe)

EXAMPLE 17:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5,6-dimethyl-1,2,3-benzotriazolyl); $R^{110}$=methoxy; n=2.

Following the procedure of Example 4, but replacing (1H)-1,2,3-triazole with 5,6-dimethyl-1H-benzotriazole, provides the desired compound. The product of Example 3 (2.0 g, 1.93 mmol), 5,6-dimethyl-1H-benzotriazole (0.852 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 18:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5,6-dimethyl-1,2,3-benzotriazolyl) and the other is hydrogen; n=2;

The title compound is isolated from the reaction described in Example 17 as a minor product.

EXAMPLE 19:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-chloro-1,2,3-benzotriazolyl); $R^{110}$=methoxy; n=2.

Following the procedure of Example 4, but replacing (1H)-1,2,3-triazole with 5-chloro-(1H)- 1,2,3-benzotriazole, provides the desired compound. The product of Example 3 (2.1 g, 2.03 mmol), 5-chloro-(1H)-1,2,3-benzotriazole (0.934 g, 6.08 mmol), and triethylamine (0.565 mL, 4.05 mmol) in 10 mL of methylene chloride are used and stirred at room temperature for three days. Semi-pure compound is isolated after silica gel column chromatography, followed by normal phase HPLC purification. The obtained product is treated with 48%-HF (4 mL) in 40 mL of acetonitrile in the procedure described in Example 5. After a normal phase-HPLC purification, the pure title compound is isolated.

EXAMPLE 20:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=, 1-(6-chloro-1,2,3-benzotriazolyl); $R^{110}$=methoxy; n=2.

The title compound is isolated from the reaction described in Example 19 as a minor product.

EXAMPLE 21:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-chloro-1,2,3-benzotriazolyl) and the other is hydrogen; n=2.

The title compound is isolated from the reaction described in Example 19 as a minor product.

EXAMPLE 22:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-chloro-1,2,3-benzotriazolyl) and the other is hydrogen; n=2.

The title compound is isolated from the reaction described in Example 19 as a minor product.

EXAMPLE 23:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-carboxy-1,2,3-benzotriazolyl); $R^{110}$=methoxy; n=2.

Following the procedure of Example 4, but replacing (1H)-1,2,3-triazole with benzotriazole-5-carboxylic acid, provides the desired compound. The product of Example 3 (2.1 g, 2.03 mmol), benzotriazole-5-carboxylic acid (0.992 g, 6.08 mmol), and triethylamine (0.565 mL, 4.05 mmol) in 10 mL of methylene chloride are used and stirred at room temperature for three days. Semi-pure compound is isolated after silica gel column chromatography, followed by normal phase HPLC purification. The obtained product is treated with 48%-HF (4 mL) in 40 mL of acetonitrile in the procedure described in Example 5. After a normal phase-HPLC purification, the pure title compound is isolated.

EXAMPLE 24:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-carboxy-1,2,3-benzotriazolyl); $R^{110}$=methoxy; n=2.

The title compound is isolated from the reaction described in Example 23 as a minor product.

EXAMPLE 25:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-carboxyl-1,2,3-benzotriazolyl) and the other is hydrogen: n=2.

The title compound is isolated from the reaction described in Example 23 as a minor product.

EXAMPLE 26:

Formula I: R=ethyl; $R^{102}$=H; $R^{103}$=hydroxy; $R^{104}$H; $R^{105}$ and $R^{106}$ taken together form an oxo; one of $R^{107}$ or $R^{108}$=methoxy and the other is hydrogen; one of $R^{109}$ or $R^{110}$ is 1-(6-carboxy-1,2,3-benzotriazolyl) and the other is hydrogen; n=2.

The title compound is isolated from the reaction described in Example 23 as a minor product.

EXAMPLE 27:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-trifluoromethyl-1,2,3-benzotriazolyl); $R^{110}$=methoxy; n=2.

Following the procedure of Example 4, but replacing (1H)-1,2,3-triazole with 5-trifluoromethyl-(1H)-1,2,3-benzotriazole, provides the desired compound. The product of Example 3 (2.1 g, 2.03 mmol), 5-trifluoromethyl-(1H)-1,2,3-benzotriazole (1.126 g, 6.08 mmol), and triethylamine (0.565 mL, 4.05 mmol) in 10 mL of methylene chloride are used and stir at room temperature for three days. Semi-pure compound is isolated after silica gel column chromatography, followed by normal phase HPLC purification. The obtained product is treated with 48%-HF (4 mL) in 40 mL of acetonitrile in the procedure described in Example 5. After a normal phase-HPLC purification, the pure title compound is isolated.

EXAMPLE 28:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-trifluoromethyl-1,2,3,-benzotriazolyl); $R^{110}$=methoxy; n=2.

The title compound is isolated from the reaction described in Example 27 as a minor product.

EXAMPLE 29:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-trifluoromethyl-1,2,3-benzotriazolyl) and the other is hydrogen; n=2.

The title compound is isolated from the reaction described in Example 27 as a minor product.

EXAMPLE 30:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-trifluoromethyl-1,2,3-benzotriazolyl) and the other is hydrogen; n=2.

The title compound is isolated from the reaction described in Example 27 as a minor product.

EXAMPLE 31:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-amino-1,2,4-triazolyl); $R^{110}$=methoxy; n=2.

Following the procedure of Example 4, but replacing (1H)-1,2,3-triazole with 3-amino-1,2,4-triazole, provides the desired compound. The product of Example 3 (2.0 g, 1.93 mmol), 3-amino-1,2,4-triazole (0.487 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 32:

Formula I; R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$or $R^{110}$ is 1-(3-amino-1,2,4-triazolyl) and the other is hydrogen; n=2.

EXAMPLE 33:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-amino-5-carboxy-1,2,4-triazolyl); $R^{110}$=methoxy; n=2.

Following the procedure of Example 4, but replacing (1H)-1,2,3-triazole with 3-amino-1,2,4-triazole- 5-carboxylic acid, provides the desired compound. The product of Example 3 (2.0 g, 1.93 mmol), 3-amino-1,2,4-triazole-5-carboxylic acid (0.742 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48 %-HF (4 mL) in 35 mL of acetonitrile in the procedure described in Example 5. After a normal phase-HPLC purification, the pure title compound is isolated.

EXAMPLE 34:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-amino-5-carboxy-1,2,4-triazolyl) and the other is hydrogen; n=2.

The title compound is isolated from the reaction described in Example 33 as a minor product.

EXAMPLE 35:

Formula I; R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-[N-maleimide]-1,2,4-triazolyl); $R^{110}$=methoxy; n=2.

Following the procedure of Example 4, but replacing (1H)-1,2,3-triazole with N-(3-triazole)maleimide, provides the desired compound. The product of Example 3 (2.0 g, 1.93 mmol), N-(3-triazole)-maleimide (0.950g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 36:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-[N-maleimide]-1,2,4-triazolyl) and the other is hydrogen; n=2.

The title compound is isolated from the reaction described in Example 35 as a minor product.

EXAMPLE 37:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-phenyl-5-ureido-1,2,4-triazolyl); $R^{110}$=methoxy; n=2.

Following the procedure of Example 4, but replacing (1H)-1,2,3-triazole with 3-phenyl-5-ureido- 1,2,4-triazole, provides the desired compound. The product of Example 3 (2.0 g, 1.93 mmol), 3-phenyl-5-ureido-1,2,4-triazole (1.177 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 38:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-phenyl-5-ureido-1,2,4-triazolyl) and the other is hydrogen; n=2.

The title compound is isolated from the reaction described in Example 37 as a minor product.

EXAMPLE 39:

Formula I; R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-[3-pyridylmethylaminol]- 1,2,4-triazolyl); $R^{110}$=methoxy; n=2.

Following the procedure of Example 4, but replacing (1H)-1,2,3-triazole with 3-(3-pyridylmethylamino)- 1,2,4-triazole, provides the desired compound. The product of Example 3 (2.0 g, 1.93 mmol), 3-(3-pyridylmethylamino)-1,2,4-triazole (1.014 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10 % methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 40: 32:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-[3-pyridylmethylaminol-1,2,4-triazolyl) and the other is hydrogen: n=2.

The title compound is isolated from the reaction described in Example 39 as a minor product.

EXAMPLE 41:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(4-methyl-1,2,3-benzotriazolyl); $R^{110}$=methoxy; n=2.

Following the procedure of Example 4, but replacing (1H)-1,2,3-triazole with tolyltriazole, provides the desired compound. The product of Example 3 (2.0 g, 1.93 mmol), tolyltriazole (0.771 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 42:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(4-methyl-1,2,3-benzotriazolyl) and the other is hydrogen; n=2.

The title compound is isolated from the reaction described in Example 41 as a minor product.

EXAMPLE 43:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-methylamino-5-phenyl-1,2,4-triazolyl); $R^{110}$=methoxy; n=2.

Following the procedure of Example 4, but replacing (1H)-1,2,3-triazole with 3-methylamino-5-phenyl- 1,2,4-triazole, provides the desired compound. The product of Example 3 (2.0 g, 1.93 mmol), 3-methylamino-5-phenyl-1, 2,4-triazole (1.009 g, 5.79 mmol), and triethylamine (0.538 mL, 3.86 mmol) in 10 mL of methylene chloride are used and stirred at room temperature for three days. Semi-pure compound is isolated after silica gel column chromatography, initally eluting with 10%-acetone in hexane, followed by 10% methanol in methylene chloride. The obtained product is treated with 48%-HF (4 mL) in 35 mL of acetonitrile in the procedure described in Example 5. After a normal phase-HPLC purification, the pure title compound is isolated.

EXAMPLE 44:

Formula I: R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-methylamino-5-phenyl-1,2,4-triazolyl) and the other is hydrogen; n=2.

The title compound is isolated from the reaction described in Example 43 as a minor product.

EXAMPLE 45:

Formula I: R=ethyl; $R^{102}$=H; $R^{103}$=hydroxy; $R^{104}$=H; $R^{105}$ and $R^{106}$ taken together form an oxo; $R^{107}$=O-fluorosulfonyl; $R^{108}$=$R^{109}$=H; $R^{110}$=methoxy; n=2.

2,6-Lutidine (0.89 mL) was added into a stirred solution of ascomycin (3.0 g) in freshly distilled (from calcium hydride) dichloromethane (30 mL) at −78° C. Fluorosulfonic art hydride (0.49 mL) in dichloromethane (10 mL) was added dropwise into the reaction mixture at −78° C. After being stirred for 1 hour, the reaction mixture was partitioned between ice-cold ether and 0.15N hydrochloric acid. The organic phase was washed once with ice-cold brine and dried over magnesium sulfate. The filtrate was poured on a silica gel column (50 g) prepacked in ether and eluted with ether. Solvent was removed in vacuo to give the title compound as light pink solid. Yield: 3.4 g; MS (FAB) m/e M+K=912.

EXAMPLE 46:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=hydroxy; $R^{110}$=methoxy; n=2.

The title compound of Example 45 (3.4 g) was dissolved in dimethylsulfoxide (25 mL) and stirred at room temperature for 2 hours. The reaction was partitioned between ethyl acetate and sodium bicarbonate. The organic phase was washed once with brine, dried over magnesium sulfate and solvent removed in vacuo. The crude product was purified by silica gel chromatography (90 g) eluting with 27% acetone/hexanes. Yield: 2.0 g, m.p.=96°–98° C.; MS (FAB) m/e M+K=830.

EXAMPLE 47:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=O-fluorosulfonyl; $R^{110}$=methoxy; n=2.

The title compound was prepared from the title compound of Example 46 and fluorosulfonic anhydride according to the procedure described in Example 45. MS (FAB) m/e M+K=912.

EXAMPLE 48:

Formula I: R=ethyl; $R^{102}$=H; $R^{103}$=hydroxy; $R^{104}$=H; $R^{105}$ and $R^{106}$ taken together form an oxo; $R^{107}$=O-trifluoromethanesulfonyl; $R^{108}$=$R^{109}$=H; $R^{110}$=methoxy; n=2.

The title compound was prepared from ascomycin and trifluoromethanesulfonyl anhydride according to the procedure described in Example 45. MS (FAB) m/e M+K=962.

EXAMPLE 49:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=O-trifluoromethanesulfonyl; $R^{110}$=methoxy; n=2.

The title compound was prepared from the title compound of Example 46 and trifluoromethanesulfonyl anhydride according to the procedure described in Example 45. MS (FAB) m/e M+K=962.

EXAMPLE 50:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-imidazolyl; $R^{110}$=methoxy; n=2.

Imidazole (0.2 g) was added into a stirred solution of the title compound of Example 45 (0.8 g) in acetone (2 mL) at 0° C. After being stirred at room temperature for 16 hours, solvent was removed in vacuo and product purified by silica gel chromatography (40 g) eluting with 6% isopropanol-dichloromethane. The product (0.7 g) was further purified by HPLC (Renin Microsorb silica gel column) eluting with 6% isopropanol-dichloromethane. Yield: 0.26 g; MS (FAB) m/e M+H=842.

EXAMPLE 51:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(2'-methylimidazolyl)]; $R^{110}$=methoxy; n=2.

The title compound is prepared from the title compound of Example 45 and 2-methylimidazole according to the procedures described in Example 50.

EXAMPLE 52:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(2'-ethylimidazolyl)]; $R^{110}$=methoxy; n=2.

The title compound is prepared from the title compound of Example 45 and 2-ethylimidazole according to the procedures described in Example 50.

EXAMPLE 53:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(2'-phenylimidazolyl)]; $R^{110}$=methoxy; n=2.

The title compound is prepared from the title compound of Example 45 and 2-phenylimidazole according to the procedures described in Example 50.

EXAMPLE 54:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(2'-methoxymethyl-imidazolyl)]; $R^{110}$=methoxy; n=2.

The title compound is prepared from the title compound of Example 45 and 2-methoxymethyl-imidazole according to the procedures described in Example 50.

EXAMPLE 55:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(2'-hydroxymethyl-imidazolyl)]; $R^{110}$=methoxy; n=2.

The title compound is prepared from the title compound of Example 45 and 2-hydroxymethyl-imidazole according to the procedures described in Example 50.

EXAMPLE 56:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(4'-methylimidazolyl)]; $R^{110}$=methoxy; n=2.

The title compound is prepared from the title compound of Example 45 and 4-methylimidazole according to the procedures described in Example 50.

EXAMPLE 57:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(4'-hydroxymethyl-imidazolyl)]; $R^{110}$=methoxy; n=2.

The title compound is prepared from the title compound of Example 45 and 4-hydroxymethyl-imidazole according to the procedures described in Example 50.

EXAMPLE 58:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(4'-cyanomethyl-imidazolyl)]; $R^{110}$=methoxy; n=2.

The title compound is prepared from the title compound of Example 45 and 4-cyanomethyl-imidazole according to the procedures described in Example 50.

EXAMPLE 59:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-(4'-bromo-imidazolyl)]; $R^{110}$=methoxy; n=2.

The tire compound is prepared from the title compound of Example 45 and 4-bromoimidazole according to the procedures described in Example 50.

EXAMPLE 60:

Formula I: R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=N-[1'-( 4'-(beta-acetylaminoethyl)-imidazolyl)]; $R^{110}$=methoxy; n=2.

The title compound is prepared from the title compound of Example 45 and N-acetylhistamine according to the procedures described in Example 50.

EXAMPLE 61:

In Vivo Assay of Biological Activity

The immunosuppressant activity of the compounds of the present invention was determined using the human mixed lymphocyte reaction (MLR) assay described by Kino, T. et al. in *Transplantation Proceedings*, XIX(5):36–39, Suppl. 6 (1987). The results of the assay, shown below in Table 1, demonstrate that the compounds tested are effective immunomodulators at sub-micromolar concentrations.

TABLE 1

| Ex. # | $IC_{50}$ (nM) |
|---|---|
| 5 | 2.48 |
| 6 | 0.44 |
| 7 | 0.21 |
| 8 | 1.76 |
| 9 | 0.23 |
| 10 | 0.22 |
| 11 | 1.56 |
| 12 | 0.94 |
| 13 | 0.62 |
| 14 | 0.07 |
| 15 | 0.04 |
| 16 | 1.00 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula

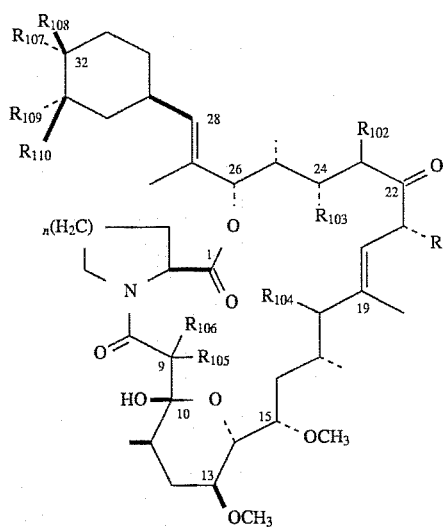

(I)

or a pharmaceutically acceptable salt, ester, amide or prodrug thereof wherein the ester selected from $C_1$-to-$C_6$ alkyl esters, $C_5$-to-$C_7$ cycloalkyl esters and arylalkyl esters and wherein the amide results from reaction of a carboxylic acid moiety in the compound of formula I with $NH_3$, $NH_2(C_1$-to-$C_6$ alkyl), $NH(C_1$-to-$C_6$ alkyl)$_2$ or a 5- or 6-membered heterocycle containing one nitrogen atom and wherein the prodrug is selected from the group consisting of (a) acyloxymethyl esters of carboxylic acids, (b) (5-methyl-2-oxo-1,3-dioxolen-4-yl)methyl esters of carboxylic acids, (c) esters derived from alcohol groups In the parent drug by reaction with succinic acid, phosphoric acid, dialkylaminoacetic acid or an amino acid (d) N-Mannich bases of amides or amines, (e) N-hydroxymethyl derivatives of amides, (f) N-acyloxyalkyl derivatives of amides or heterocyclic amines, (g) oxazolidinones derived from ketone groups in the parent drug by reaction with 2-aminoethanol, N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol and (h) enol esters derived from ketone groups In the parent drug, wherein n is an integer between one and three;

R is selected from the group consisting of methyl, ethyl, allyl and propyl;

$R^{102}$ is hydrogen and $R^{103}$ is selected from the group consisting of hydrogen, hydroxy and protected hydroxy wherein the hydroxy protecting group is selected from methylthiomethyl, dimethylthexylsilyl, tri($C_1$-to-$C_8$-alkyl)silyl, $C_1$-to-$C_8$-alkyldiarylsilyl, triarylsilyl, tri-(aryl-$C_1$-to-$C_{12}$-alkyl)silyl, $C_1$-to-$C_{12}$-alkyl-C(O)-, aryl-C(O)-, $C_1$-to-$C_8$-alkyl-O-C(O)-, $C_1$-to-$C_8$-alkyl-S(O)$_2$- and aryl-S(O)$_2$-, or, taken together, $R^{102}$ and $R^{103}$ form a bond;

$R^{104}$ is selected from the group consisting of hydrogen, hydroxy and protected hydroxy independently defined as above;

$R^{105}$ and $R^{106}$ are selected such that one of $R^{105}$ and $R^{106}$ is hydrogen and the other is hydroxy, or, taken together, $R^{105}$ and $R^{106}$ form a divalent radical selected from the group consisting of oxygen and methylene;

$R^{107}$, $R^{108}$ and $R^{110}$ are each independently selected from the group consisting of hydrogen, methoxy and an azole radical; and $R^{109}$ is selected from the group consisting of hydrogen and an azole radical, with the provisos that (a) exactly one of $R^{107}$, $R^{108}$, $R^{109}$ and $R^{110}$ is an azole radical, (b) exactly one of $R^{107}$ and $R^{108}$ is hydrogen, and (c) exactly one of $R^{109}$ and $R^{110}$ is hydrogen;

where the azole radical is selected from the group consisting of

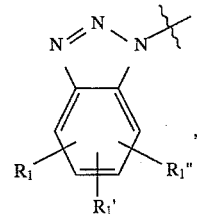

(II)

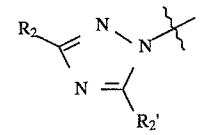

(III)

and

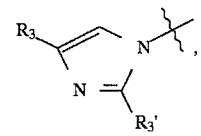

(IV)

where $R^1$, $R^{1'}$ and $R^{1''}$ are independently selected from the group consisting of
(i) hydrogen,
(ii) $C_1$-to-$C_8$-lower alkyl,
(iii) $C_2$-to-$C_8$-lower alkenyl,
(iv) $C_3$-to-$C_8$-cycloalkyl,
(v) $C_3$-to-$C_8$-cycloalkyl-$C_1$-to-$C_8$-alkyl,
(vi) $C_3$-to-$C_8$-cycloalkyl-$C_2$-to-$C_{12}$-alkenyl,
(vii) nitro,
(viii) halogen,
(ix) —C(O)—O—$R^4$ where $R^4$ is selected from the group consisting of
  (a) hydrogen,
  (b) $C_1$-to-$C_8$-lower alkyl, and
  (c) aryl-$C_1$-to-$C_{12}$-alkyl,
(x) mono-, di-, tri-, or perhalogenated $C_1$-to-$C_8$-lower-alkyl,
(xi) aryl, and
(xii) aryl-$C_1$-to-$C_{12}$-alkyl;

or, taken together, any two adjacent $R^1$, $R^{1'}$ and $R^{1''}$ and the carbon atoms to which they are attached form a saturated or unsaturated carbocyclic or heterocyclic ring having between five and seven ring atoms;

$R^2$ and $R^{2'}$ are independently selected from the group consisting of
(i) hydrogen,
(ii) $C_1$-to-$C_8$-lower alkyl,
(iii) $C_2$-to-$C_8$-lower alkenyl,
(iv) amino,
(v) $C_1$-to-$C_8$-alkylamino,
(vi) aryl-$C_1$-to-$C_{12}$-alkylamino,
(vii) acylamino wherein acyl is $C_1$-to-$C_{12}$-C(O)- or aryl-C(O)-,
(viii) arylamino,
(ix) $C_3$-to-$C_8$-cycloalkyl,
(x) $C_3$-to-$C_8$-cycloalkyl-$C_1$-to-$C_8$-alkyl,
(xi) $C_3$-to-$C_8$-Cycloalkyl-$C_2$-to-$C_{12}$-alkenyl,
(xii) —C(O)—O—$R^4$ where $R^4$ is as described above,
(xiii) ureido,
(xiv) aryl, (xv) aryl-$C_1$-to-$C_{12}$-alkyl,
(xvi) heterocyclic-$C_1$-to-$C_{12}$-alkylamino, and
(xvii) nitro;

and $R^3$ and $R^{3'}$ are independently selected from the group consisting of
(i) hydrogen,
(ii) $C_1$-to-$C_8$-lower alkyl,
(iii) hydroxy-$C_1$-to-$C_{12}$-alkyl,
(iv) $C_1$-to-$C_8$-alkoxy-$C_1$-to-$C_{12}$-alkyl,
(v) halogen,
(vi) cyano-$C_1$-to-$C_{12}$-alkyl,
(vii) acylamino-$C_1$-to-$C_{12}$-alkyl wherein acyl is independently defined as above,
(viii) $C_1$-to-$C_8$-alkylamino,
(ix) aryl-$C_1$-to-$C_{12}$-alkylamino,
(x) acylamino wherein acyl is independently defined as above,
(xi) arylamino,
(xii) $C_3$-to-$C_8$-cycloalkyl,
(xiii) $C_3$-to-$C_8$-cycloalkyl-$C_1$-to-$C_8$-alkyl,
(xiv) aryl, and
(xv) arylalkyl;

wherein at each occurrence the term aryl is independently selected from phenyl, 1- or 2-naphthyl, fluorenyl, (1,2)-dihydronaphthyl, (1,2,3,4)-tetrahydronaphthyl, indenyl, indanyl; and wherein at each occurrence the term heterocyclic is independently selected from pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrimidinyl, pyridazinyl, xanthenyl, xanthonyl, xanthopterinyl, oxazoyl, oxaxolidinyl, thiouracilyl, isoxaxolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thyminyl, benzimidazoly, benzothiazolyl, benzoxazolyl, furyl, thienyl and benzothienyl.

2. A compound according to claim 1 wherein R is ethyl.
3. A compound according to claim 1 wherein $R^{102}$ is hydrogen.
4. A compound according to claim 1 wherein $R^{103}$ is selected from the group consisting of hydrogen and hydroxy.
5. A compound according to claim 1 wherein $R^{103}$ is protected hydroxy.
6. A compound according to claim 1 wherein $R^{104}$ is hydrogen or hydroxy.
7. A compound according to claim 1 wherein $R^{105}$ and $R^{106}$, taken together, are oxo.
8. A compound according to claim 1 wherein n is one or two.
9. A compound according to claim 1 wherein the heterocyclic radical is a 1,2,3-benztriazole radical having the formula:

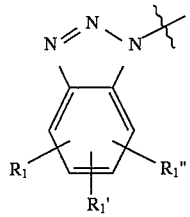

wherein $R_1$, $R_{1'}$ and $R_{1''}$ are as defined therein.

10. A compound according to claim 1 wherein the heterocyclic radical is a 1,2,4-triazole radical having the formula:

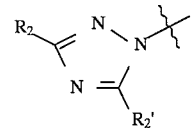

wherein $R_2$ and $R_{2'}$ are as defined therein.

11. A compound according to claim 10, wherein $R^2$ and $R^{2'}$ are each hydrogen.
12. A compound according to claim 1 of the formula:

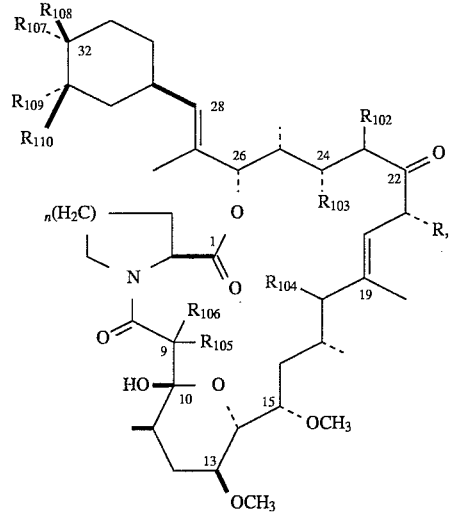

wherein R=ethyl; $R^{102}$=H; $R^{103}$=tert-butylidimethylsilyloxy; $R^{104}$=H; $R^{105}$ and $R^{106}$ taken together form an oxo; $R^{107}$=$R^{109}$=H; $R^{108}$=1-(1,2,3-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,3-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(1,2,3-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-nitro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-nitro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-nitro-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-nitro-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(1,2,4-triazolyl) and the other is hydrogen; and n=2;

T=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-nitro-1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-nitro-1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5,6-dimethyl-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5,6-dimethyl-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-chloro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-chloro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-chloro-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-chloro-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-carboxy-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-carboxy-1,2,3-benzotriazolyl); $R^{110}$=methoxy; and n=2;

R=ethyl; $R^{102}$H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-carboxy-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-carboxy-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-trifluoromethyl-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-trifluoromethyl-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(5-trifluoromethyl-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(6-trifluoromethyl-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-amino-1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-amino-1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-amino-5-carboxy-1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-amino-5-carboxy-1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-[N-maleimide]-1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-[N-maleimide]-1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-phenyl-5-ureido-1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-phenyl-5-ureido-1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-[3-pyridylmethylamino]-1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(3-[3-pyridylmethylamino]-1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(4-methyl-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$=methoxy and the other is hydrogen; one of $R^{109}$ or $R^{110}$ is 1-(4-methyl-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3- methylamino-5-phenyl-1,2,4-triazolyl); $R^{110}$=methoxy; and n=2; and

R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(3-methylamino-5-phenyl-1,2,4-triazolyl) and the other is hydrogen; n=2.

13. A compound according to claim 1 of the formula:

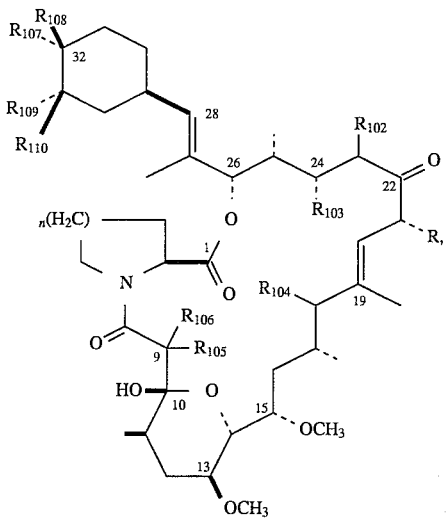

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,3-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(1,2,3-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-nitro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(5-nitro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(6-nitro-1,2,3-benzotriazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(5-nitro-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(6-nitro-1,2,3-benzotriazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(1,2,4-triazolyl); $R^{110}$=methoxy; and n=2;

R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(1,2,4-triazolyl) and the other is hydrogen; and n=2;

R=ethyl; $R^{102}$=H; $R^{103}$=hydroxy; $R^{104}$=H; $R^{105}$ and $R^{106}$ taken together form an oxo; $R^{107}$=$R^{109}$=H; $R^{108}$=1-(3-nitro-1,2,4-triazolyl); $R^{110}$=methoxy; and n=2; and R=ethyl; $R^{102}$=H; $R^{103}$=hydroxy; $R^{104}$=H; $R^{105}$ and $R^{106}$ taken together form an oxo; one of $R^{107}$ or $R^{108}$= methoxy and the other is hydrogen; one of $R^{109}$ or $R^{110}$ is 1-(3-nitro-1,2,4-triazolyl) and the other is hydrogen; and n=2.

14. A pharmaceutical composition useful for immunomodulation, comprising a therapeutically effective amount of a compound according to claim 1 in combination with a pharmaceutically acceptable carrier.

15. A pharmaceutical composition useful for immunomodulation, comprising a therapeutically effective amount of a compound according to claim 10 in combination with a pharmaceutically acceptable carrier.

16. A pharmaceutical composition useful for immunomodulation, comprising a therapeutically effective amount of a compound according to claim 13 in combination with a pharmaceutically acceptable carrier.

17. A method of producing immunomodulation in a patient in need of such treatment, comprising administering to the patient a therapeutically effective amount of a compound according to claim 1.

18. A method of producing immunomodulation in a patient in need of such treatment, comprising administering to the patient a therapeutically effective amount of a compound according to claim 10.

19. A method of producing immunomodulation in a patient in need of such treatment, comprising administering to the patient a therapeutically effective amount of a compound according to claim 13.

* * * * *

UNITED STATES PATENT AND TRADEMARK OFFICE
CERTIFICATE OF CORRECTION

PATENT NO. : 5,541,193
DATED : July 30, 1996
INVENTOR(S) : M. Kawai, et. Al.

It is certified that error appears in the above-indentified patent and that said Letters Patent is hereby corrected as shown below:

Column 33, line 22, change "ester" to --ester is--.

Column 33, line 31, change "In" to --in--.

Column 33, line 42, change "In" to --in--.

Column 34, line 28, change "$R^1$, $R^{1'}$ and $R^{1''}$." to --$R^1$, $R^{1'}$ and $R^{1''}$--.

Column 34, line 47, change "$R^1$, $R^{1'}$ and $R^{1''}$." to --$R^1$, $R^{1'}$ and $R^{1''}$--.

Column 34, line 51, change "$R^{2'}$" to --$R^{2'}$--.

Column 35, line 4, change "$R^{3'}$" to --$R^{3'}$--.

Column 35, line 36, change "isothiazolldinyl" to --isothiazolidinyl--.

UNITED STATES PATENT AND TRADEMARK OFFICE
CERTIFICATE OF CORRECTION

PATENT NO. : 5,541,193
DATED : July 30, 1996
INVENTOR(S) : M. Kawai, et. Al.

It is certified that error appears in the above-indentified patent and that said Letters Patent is hereby corrected as shown below:

Column 36, line 20, change "R," to --R--.

Column 37, line 9, change "T=ethyl" to --R=ethyl--.

Column 37, line 51, change "$R^{102}H$" to --$R^{102}=H$--.

Column 39, delete lines 51-53.

Signed and Sealed this

Twenty-fourth Day of December, 1996

*Attest:*

BRUCE LEHMAN

*Attesting Officer*     Commissioner of Patents and Trademarks